United States Patent
Tartaglia

(12) 
(10) Patent No.: US 6,391,964 B1
(45) Date of Patent: May 21, 2002

(54) AQUEOUS NAIL POLISH COMPOSITIONS

(76) Inventor: Joseph John Tartaglia, 2380 S. Window Rock Pl., Tuscon, AZ (US) 85710

( * ) Notice: Subject to any disclaimer, the term of this patent is extended or adjusted under 35 U.S.C. 154(b) by 0 days.

(21) Appl. No.: 09/676,574

(22) Filed: Oct. 2, 2000

(51) Int. Cl.$^7$ .......................... C08L 31/04; C08L 75/04; A61K 7/043; B65D 77/00
(52) U.S. Cl. ...................... 524/803; 524/501; 524/591; 524/832; 424/61; 206/568; 206/581
(58) Field of Search .................................. 524/501, 591, 524/803, 832; 424/61; 206/568, 581

(56) References Cited

U.S. PATENT DOCUMENTS

| | | | |
|---|---|---|---|
| 4,158,053 A | * | 6/1979 | Greene et al. |
| 4,892,787 A | * | 1/1990 | Kruse et al. |
| 5,746,814 A | * | 5/1998 | Malhoera et al. |
| 6,120,202 A | * | 9/2000 | Donsky |
| 6,136,300 A | * | 10/2000 | Ellingson et al. |

* cited by examiner

*Primary Examiner*—Tae H. Yoon
(74) *Attorney, Agent, or Firm*—Evelyn M. Sommer

(57) ABSTRACT

A system of aqueous nail polish compositions is provided, including base coat, color coat, and top coat formulations. The base coat formulation comprises aqueous emulsions of acrylic polymer and vinyl acetate/acrylic copolymer. The color coat formulation comprises an aqueous solution of polyurethane resin and a colorant in addition to aqueous emulsions of acrylic polymer and vinyl acetate/acrylic polymer. Finally, the top coat formulation comprises an aqueous emulsion of vinyl acetate/acrylic polymer and an aqueous solution of polyurethane resin. The aqueous nail polish formulations of the present invention are substantially non-flammable and non-toxic while providing comparable nail coverage, wearability, and stability to non-aqueous nail polishes. Further, the present formulations offer rapid dry times and may be readily applied to nails using conventional nylon brushes.

12 Claims, No Drawings

AQUEOUS NAIL POLISH COMPOSITIONS

BACKGROUND OF THE INVENTION

The invention relates to the general field of clear and pigmented coatings applied to human nails. In particular, the invention relates to nail polish compositions that are water-based and substantially non-flammable and non-toxic. More particularly the present invention relates to nail polish compositions and kits formed therefrom.

DESCRIPTION OF THE PRIOR ART

Nail polishes (including clear base and top coats), lacquers and enamels comprise a class of products regularly used by modern women as part of their beauty care regimen and particularly to enhance their nails or protect their nails from everyday conditions and stresses. Typically, the process of applying nail polish includes application of three to four layers of coatings, each of which is allowed to dry. For example, one may first apply a layer of clear base coat followed by two layers of color enamel and, finally, a layer of clear top coat for gloss and protection. Commercially-available nail polishes employ a plurality of volatile organic elements compounds such as butyl acetate, toluene, nitrocellulose, an amyl-sulfonamide formaldehyde resin and isopropyl alcohol as a non-aqueous solvent base. These compounds are readily combustible and highly toxic, thereby rendering non-aqueous nail polishes hazardous to humans and to the environment and require long drying times due to the slow evaporating solvents used in the formulations.

The unavailability of a less toxic, non-inflammable alternative to traditional nail polishes is due at least in part to the difficulty of maintaining the quality of appearance as well as the convenience offered by non-aqueous polishes. Traditional non-aqueous polish formulations are easily applied using a nylon brush and provide good, uniform coverage of the nail with rapid drying of each coat. Moreover, traditional polishes are abrasion-resistant.

There remains a need for nail polish formulations (including base, color, and top coats) that are substantially non-flammable and non-toxic while also offering uncompromised nail coverage, drying time, stability, and wearability. The nail polish should be readily applied by brush for ease of application and should be relatively quick to dry, provide good wear, adhesion and gloss.

SUMMARY OF THE INVENTION

Accordingly, aqueous nail polish formulations and a system of such nail polishes are provided that are substantially non-flammable and non-toxic while offering good nail coverage, wear-resistance, good wear adhesion, gloss and stability. Moreover, the present nail polish formulations are quick drying and may be applied to the nails using conventional nylon brushes. In sum, these formulations overcome the disadvantages of non-aqueous nail polishes while maintaining their quality of appearance and convenience of use.

The present system of aqueous nail coating compositions or polishes includes a base coat, a color coat, and a top coat formulation. The base coat formulation comprises aqueous emulsions of acrylic polymer and vinyl acetate/acrylic copolymer. The color coat formulation comprises an aqueous solution of polyurethane resin and a colorant in addition to aqueous emulsions of acrylic polymer and vinyl acetate/acrylic polymer. Finally, the top coat formulation comprises an aqueous emulsion of vinyl acetate/acrylic polymer and an aqueous solution of polyurethane resin. All of these materials are readily available commercially.

The present nail polish formulations offer an environmentally-friendly alternative to conventional non-aqueous nail polishes without an associated sacrifice in quality. Additionally, these formulations do not require the use of a highly toxic and highly flammable nail polish remover, but may be simply peeled off the nail. Therefore, the formulations of the present invention enable one to avoid the toxic fumes and potential fire hazard associated with both the application and the removal of non-aqueous nail polishes.

DETAILED DESCRIPTION OF THE INVENTION

The present nail polish formulations are substantially nonflammable and non-toxic while offering good nail coverage, long wear, uniformity of application, quick drying times, stability, and abrasion-resistance. The nail polish formulations may be applied to the nail using conventional nylon brushes in the same manner by which non-aqueous nail polishes are typically applied. Thus, the present formulations offer a safer alternative to non-aqueous nail polishes while maintaining good cosmetic appearance and the conveniences of rapid drying and brushed-on application.

As used herein, the term "nail polish" is a comprehensive term describing a nail polish composition (including coloring products) system, kit or the like, which is useful for providing, for example, aesthetic or prophylactic benefits to the nail.

The nail polish system of the present invention includes a base coat formulation, a color coat formulation, and a top coat formulation. For optimum wear-resistance and cosmetic appeal, it is contemplated that one would apply a first layer of the base coat formulation to the nails followed by one or two layers of the color coat formulation and finally topped by a layer of the top coat formulation. The base coat is intended to provide a uniform layer across the nail to enhance adhesion of the subsequent color coats as well as their uniform coverage of the nail. The top layer is applied to protect the color layers and to add a finishing gloss to the nail color. Each of the formulations dries quickly, on the order of less than one minute or about fifty seconds.

The system or kits of the invention preferably comprise a base coat composition, a mid coat or color composition and a top coat composition. Optionally, the kits can comprise a base coat composition and a color composition or color composition and top coat composition. If color is not desired the kit can comprise a base coat and top coat composition.

Advantageously, the present nail polish formulations may be readily removed from the nail by simply peeling off the nail polish layers. In contrast, non-water based lacquers and enamels must be removed using nail-polish removers containing volatile organic chemicals that are toxic and flammable. It is noted that if the present nail polish formulations are applied to acrylic nails rather than directly onto a human nail, the present nail polish formulations will not readily peel off and must instead be removed using a nail-polish remover.

At the outset, it is noted that these water-based nail polish formulations do not perform well in combination with oil-based or lacquer-type nail polish products. Thus, the present water-based base coat should not, for example, be employed as a base coat underlying a lacquer nail polish. The present base, color, and top nail polish formulations are intended for use in combination with each other or with other water-based nail polish formulations.

The base coat formulation comprises a binder and a hardener. The binder is an aqueous emulsion of acrylic polymer, such as is commercially available under the trade designations NEOCRYL A-655 and NEOCRYL XK90 from Zeneca of Wilmington, Mass. The hardener is an aqueous emulsion of vinyl acetate/acrylic copolymer, such as is commercially available under the trade designations of POLYCO® 2152 and POLYCO® 2149AD from Rohm & Haas Co. of Philadelphia, Pa. and NEOCRYL XK90 from Zeneca. The hardener Component also serves to increase the dry time of the base coat. Preferably, the base coat comprises NEOCRYL A-655 and at least one of the POLYCO® 2152 emulsion and the POLYCO® 2149AD (aqueous emulsion of vinyl acetate/acrylic copolymer).

NEOCRYL A-655 comprises an aqueous emulsion of acrylic polymer having a proprietary composition including an amount of acrylic polymer not exceeding about 50 wt %, water, and a small amount of ammonia. This emulsion will not support combustion unless the associated water has substantially evaporated. It is also substantially non-toxic, with its toxicity deriving only from its low level of ammonia. Throughout the specification, the present nail polish formulations are characterized as being substantially non-toxic, although the formulations contain relatively low levels of chemicals of various toxicities. It is presumed that one skilled in the art would understand that the level of toxicity of the present water-based formulations is almost negligible in comparison to that of conventional non-aqueous nail polish formulations having substantial concentrations of volatile organic chemicals. Hence, it is believed appropriate to characterize the present formulations as substantially non-toxic.

The POLYCO® 2149AD and POLYCO® 2152 emulsions each comprise (a) about 47 to 48 wt % vinyl acetate/acrylic copolymer; (b) about 0.09 wt % (maximum) vinyl acetate; (c) about 0.095 wt % acetaldehyde; (d) <0.1 wt % aqua ammonia; and (e) the balance, or about 52 to 53 wt %, water. These emulsions are substantially non-flammable and exhibit only slight toxicity. The emulsions are each in the form of a milky white liquid and have a vinyl acetate odor. The POLYCO® 2152 differs from the POLYCO® 2149AD only by having a larger particle size.

The binder, in the form of an aqueous emulsion of acrylic polymer, is present in the base coat at a concentration within the range of about 2.25 to 3.75 parts by volume. The hardener, in the form of an aqueous emulsion of vinyl acetate/acrylic copolymer, is present at a concentration within the range of about 0.75 to 1.33 parts by volume. If the base coat employs concentrations outside of these ranges, it has a tendency to crystallize and to have a tacky finish. Preferably, the base coat comprises about 3 parts by volume binder and about 1 part by volume hardener. Most preferably, the base coat comprises about 3 parts by volume NEOCRYL A-655 (aqueous emulsion of acrylic polymer) and about 1 part by volume of at least one of the POLYCO® 2152 and the POLYCOL® 2149AD (Aqueous emulsions of vinyl acetate/acrylic copolymer). A particularly preferred base coat formulation comprises 3 parts NEOCRYL A-655, 1 part NEOCRYL XK90 and ½ part NEOCRYL R-967.

The base coat is prepared by combining the components in any order and then mixing them together, such as by a mechanical mixer or by manually stirring the mixture Turning now to the color coat formulation, it comprises a hardener, a binder, a component for adding gloss and wear-resistance and a colorant. The hardener and binder essentially are the same materials as employed in the base coat. More particularly, the hardener/dryer is an aqueous emulsion of vinyl acetate/acrylic copolymer, such as is commercially available under the trade designations of POLYCO® 2152 and POLYCO® 2149AD, as described above. The binder is an aqueous emulsion of acrylic polymer, such as is commercially available under the trade designation NEOCRYL A655, also described above in connection with the base coat.

The component for adding gloss and wear-resistance to the color coat is an aqueous solution of polyurethane resin, such as is commercially available under the trade designation RESISTHANE® from The HYDROCOTE® Company, Inc. of Tennent, N.J. RESISTHANE® comprises (a) about 35 to 40 wt % polyurethane resin; (b) about 7.5 wt % 2-butoxy ethanol; (c) about 5 wt % diethylene glycol monobutyl ether; (d) about 1 to 5 wt % isopropanol: (e) about 1 wt % triethylamine; and (e) the balance, or about 45 to 50 wt %, water. This material is substantially non-flammable—it will not support combustion unless the water component has evaporated. Further, it is also substantially non-toxic, with only a slight toxicity deriving from its low concentrations of 2-butoxy ethanol, isopropanol, and triethylamine. This material is in liquid form and is water white in appearance. NEORES R-967 from Zeneca and POLY-SHIELD GLOSS SATIN from the HYDROCOTE company, inc., are other examples of polyurethane products which can be used in the practice of the invention.

The colorant employed in the practice of the invention is water-based in form, such as a water-based pigment dispersion. It is contemplated that any water-based pigment dispersion may be employed in the practice of the invention, so long as it is safe for use in a nail polish. It is further contemplated that blends of various water-based pigment dispersions will be used to generate a variety of nail polish colors. One commercial source of water-based pigment dispersions is Engelhard Corp. of Louisville, Ky. For example, an Engelhard water-based pigment dispersion commercially known as Gallery One G1-F Red Oxide is suitable for use in the present formulation and comprises: (a) about 50 to 65 wt % C.I. Pigment Red 101; (b) about 5 to 15 wt % each of diethylene glycol and ethylene glycol; (c) about 5 to 15 wt % water; (d) about 1 to 5 wt % ethoxylated nonyl phenol; and (e) about 1 to 5 wt % proprietary surfactants. Another example is an Engelhard water-based pigment dispersion commercially known as Gallery One G1-E Phthalo Blue, which comprises (a) about 5 to 15 wt % C.I. Pigment Blue 15:2; (b) about 10 to 20 wt % each of diethylene glycol and ethylene glycol; (c) about 10 to 20 wt % water; (d) about 1 to 5 wt % ethoxylated nonyl phenol; and (e) about 25 to 40 wt % magnesium silicate.

Preferably, the color coat formulation comprises the following: (a) at least one of the POLYCO® 2152 and the POLYCO® 2149AD (aqueous emulsions of vinyl acetate/acrylic copolymer) as a hardener/dryer; (b) NEOCRYL A-655 as a binder; (c) RESISTHANE (aqueous solution of polyurethane resin) a gloss and wear-resistance component; and (d) a water-based pigment dispersion.

The hardener, in the form of an aqueous emulsion of vinyl acetate/acrylic copolymer, is present in the color coat at a concentration within the range of about 3.25 to 4.75 parts by volume. The binder, in the form of an aqueous emulsion of acrylic polymer, is present in the color coat at a concentration within the range of about 1.5 to 2.5 parts by volume. The glossy/wear-resistant component, in the form of an aqueous solution of polyurethane resin, is present in the color coat at a concentration within the range of about 0.5 to 3.75 parts by volume. Preferably, the color coat comprises roughly 1 part by volume color solution. It is considered a routine endeavor for one having ordinary skill in the art to determine an appropriate concentration at which to add colorant to a base.

Preferably, the color coat formulation comprises about 4 parts by volume hardener; about 2 parts by volume binder; about 2 parts by volume glossy/wear-resistant component; and about 1 part by volume color solution. Most preferably, the color coat comprises about 4 parts by volume of at least one of the POLYCO® 2152 and 2149AD (aqueous emulsions of vinyl acetate/acrylic copolymer); about 2 parts by volume NEOCRYL A-655 (aqueous emulsion of acrylic polymer); about 2 parts by volume (RESISTHANE) (aqueous solution of polyurethane resin); and about 1 part by volume of at least one water-based pigment dispersion, such as available from Engelhard Corp.

A particularly preferred color coat formulation comprises 4 parts NEOCRYL A-655, 3 parts NEOCRYL XK90, 1 part NEORES R-967, ¼ part POLYCO-2149 AD and 1 part of the colorant described above. Like the base coat formulation, the color coat formulation is prepared by combining the components in any order and then mixing them together, such as by a mechanical mixer or by manually stirring the mixture.

The top coat formulation comprises a glossy, wear-resistant component as well as a hardener. The wear-resistant component is an aqueous solution of polyurethane resin, such as is commercially available under the trade designation RESISTHANE® as described above in connection with the color coat formulation. The hardener/dryer component is an aqueous emulsion of vinyl acetate/acrylic copolymer, such as is commercially available under the trade designations of POLYCO® 2152 and POLYCO® 2149AD as described above in connection with the base coat. The hardener component also serves to increase the dry time of the top coat. Preferably, the top coat comprises RESISTHANE® and at least one of the POLYCO® 2152 and POLYCO® 2149AD (aqueous emulsions of vinyl acetate/acrylic copolymer).

The wear-resistant component, in the form of an aqueous solution of polyurethane resin, is present in the top coat at a concentration within the range of about 2.5 to 3.75 parts by volume. The hardener, in the form of an aqueous emulsion of vinyl acetate/acrylic copolymer, is present at a concentration within the range of about 0.75 to 1.25 parts by volume. If the top coat employs an excessive amount of hardener, the top coat finish is cloudy and streaky. Preferably, the top coat comprises about 3 parts by volume of the aqueous polyurethane resin and 1 part by volume of aqueous emulsion of vinyl acetate/acrylic copolymer. Most preferably, the base coat comprises about 3 parts by volume of RESISTHANE® (aqueous solution of polyurethane resin) and about 1 part by volume of at least one of the POLYCO® 2152 and POLYCO® 2149AD (aqueous emulsions of vinyl acetate/acrylic copolymer). A particularly preferred top coat formulation comprises 3 parts POLYSHIELD GLOSS SATIN and 1 part POLYCO 2149 AD. The top coat is prepared by combining the components in any order and then mixing them together, such as by a mechanical mixer or by manually stirring the mixture.

The kits herein are comprised of two or more separate and different compositions, most preferably two or three different compositions which are preferably a base coat composition and a mid coat or color coat composition and/or a top coat composition. Most preferably the kits are comprised of a base coat composition, a mid coat or color composition and a top coat composition.

Frequently children use nail polish and for all of the reasons set out above, parents are hesitant to permit such use. Because of the advantageous properties of the water based formulations of the invention, such use by children need no longer be discouraged. The base and top coats or any one of them can be as described above and a color coat formulation of 4 parts NEOCRYL A-655, 3 parts NEOCRYL XK90, 1 part NEORES R-967 and a suitable colorant for children.

Thus, there has been disclosed herein a system of nail polish formulations. It will be readily apparent to those skilled in the art that various changes and modifications of an obvious nature may be made without departing from the spirit of the invention, and all such changes and modifications are considered to fall within the scope of the invention as defined by the appended claims.

What is claimed is:

1. A system of aqueous nail polish composition comprising:
   (a) an aqueous base-coat nail polish composition comprising:
      (i) an aqueous emulsion of acrylic polymer,
      (ii) an aqueous emulsion of vinyl acetate/acrylic copolymer,
   (b) an aqueous color nail polish composition comprising:
      (i) an aqueous emulsion of acrylic polymer,
      (ii) an aqueous emulsion of vinyl acetate/acrylic copolymer,
      (iii) an aqueous solution of polyurethane resin, and
      (iv) a colorant.
   (c) an aqueous top-coat nail polish composition comprising:
      (i) an aqueous solution of polyurethane resin, and
      (ii) an aqueous emulsion of vinyl acetate/acrylic copolymer.

2. The system of nail polish compositions of claim 1 comprising:
   (a) an aqueous base-coat nail polish composition comprising:
      (i) about 2.25 to 3.75 parts by volume of aqueous emulsion of acrylic polymer, and
      (ii) about 0.75 to 1.33 parts by volume of aqueous emulsion of vinyl acetate/acrylic copolymer;
   (b) an aqueous color-coat nail polish composition comprising:
      (i) about 1.5 to 2.5 parts by volume of aqueous emulsion of acrylic polymer,
      (ii) about 3.25 to 4.75 parts by volume of aqueous emulsion of vinyl acetate/acrylic copolymer,
      (iii) about 0.5 to 2.75 parts by volume of aqueous solution of polyurethane resin, and
      (iv) a colorant; and
   (c) aqueous top-coat nail polish composition comprising:
      (i) about 2.5 to 3.75 parts by volume of aqueous solution of polyurethane resin, and
      (ii) about 0.75 to 1.25 parts by volume of aqueous emulsion of vinyl acetate/acrylic copolymer.

3. The system of aqueous nail polish compositions of claim 2 comprising:
   (a) an aqueous base-coat nail polish composition comprising:
      (i) about 3 parts by volume of aqueous emulsion of acrylic polymer,
      (ii) about 1 part by volume of aqueous emulsion of vinyl acetate/acrylic copolymer,
   (b) an aqueous color-coat nail polish composition comprising:

(i) about 2 parts by volume of aqueous emulsion of acrylic polymer,
(ii) about 4 parts by volume of aqueous emulsion of vinyl acetate/acrylic copolymer,
(iii) about 2 parts by volume of aqueous solution of polyurethane resin, and
(iv) a colorant; and
(c) aqueous top-coat nail polish composition comprising:
(i) about 3 parts by volume of aqueous solution of polyurethane resin, and
(ii) about 1 part by volume of aqueous emulsion of vinyl acetate/acrylic copolymer.

4. The system of aqueous nail polish compositions of claim 1 wherein at least one of the following conditions obtains:
(a) said aqueous emulsion of acrylic polymer includes acrylic polymer in an amount not exceeding about 50 wt %;
(b) said aqueous emulsion of vinyl acetate/acrylic copolymer includes about 47 to 48 wt % vinyl acetate/acrylic copolymer and about 52 to 53 wt % water; and
(c) said aqueous solution of polyurethane resin includes about 35 to 40 wt % polyurethane resin.

5. A system of aqueous nail polish compositions, comprising:
(a) an aqueous base-coat nail polish composition comprising:
(i) an aqueous emulsion of acrylic polymer, and
(ii) an aqueous emulsion of vinyl acetate/acrylic copolymer; and
(b) an aqueous color-coat nail polish composition comprising:
(i) an aqueous emulsion of acrylic polymer,
(ii) an aqueous emulsion of vinyl acetate/acrylic copolymer,
(iii) an aqueous solution of polyurethane resin, and
(iv) a colorant.

6. The system of nail polish compositions of claim 5 comprising:
(a) an aqueous base-coat nail polish composition comprising:
(i) about 2.25 to 3.75 parts by volume of aqueous emulsion of acrylic polymer, and
(ii) about 0.75 to 1.33 parts by volume of aqueous emulsion of vinyl acetate/acrylic copolymer;
(b) an aqueous color-coat nail polish composition comprising:
(i) about 1.5 to 2.5 parts by volume of aqueous emulsion of acrylic polymer,
(ii) about 3.25 to 4.75 parts by volume of aqueous emulsion of vinyl acetate/acrylic copolymer,
(iii) about 0.5 to 2.75 parts by volume of aqueous solution of polyurethane resin, and
(iv) a colorant.

7. The system of aqueous nail polish compositions of claim 6 comprising:
(a) an aqueous base-coat nail polish composition comprising:
(i) about 3 parts by volume of aqueous emulsion of acrylic polymer,
(ii) about 1 part by volume of aqueous emulsion of vinyl acetate/acrylic copolymer,
(b) an aqueous color-coat nail polish composition comprising:
(i) about 2 parts by volume of aqueous emulsion of acrylic polymer,
(ii) about 4 parts by volume of aqueous emulsion of vinyl acetate/acrylic copolymer,
(iii) about 2 parts by volume of aqueous solution of polyurethane resin, and
(iv) a colorant.

8. The system of nail polish compositions of claim 5 wherein at least one of the following conditions obtains:
(a) said aqueous emulsion of acrylic polymer includes acrylic polymer in an amount not exceeding about 50 wt %;
(b) said aqueous emulsion of vinyl acetate/acrylic copolymer includes about 47 to 48 wt % vinyl acetate/acrylic copolymer and about 52 to 53 wt % water; and
(c) said aqueous solution of polyurethane resin includes about 35 to 40 wt % polyurethane resin.

9. A system of aqueous nail polish compositions comprising:
(a) an aqueous base-coat nail polish composition comprising:
(i) an aqueous emulsion of acrylic polymer, and
(ii) an aqueous emulsion of vinyl acetate/acrylic copolymer; and
(b) aqueous top-coat nail polish composition comprising:
(i) an aqueous solution of polyurethane resin, and
(ii) an aqueous emulsion of vinyl acetate/acrylic copolymer.

10. The system of aqueous nail polish compositions of claim 9 comprising:
(a) an aqueous base-coat nail polish composition comprising:
(i) about 2.25 to 3.75 parts by volume of aqueous emulsion of acrylic polymer, and
(ii) about 0.75 to 1.33 parts by volume of aqueous emulsion of vinyl acetate/acrylic copolymer;
(b) aqueous top-coat nail polish composition comprising:
(i) about 2.5 to 3.75 parts by volume of aqueous solution of polyurethane resin, and
(ii) about 0.75 to 1.33 parts by volume of aqueous emulsion of vinyl acetate/acrylic copolymer.

11. The system of aqueous nail polish compositions of claim 9 comprising:
(c) an aqueous base-coat nail composition comprising:
(i) about 3 parts by volume of aqueous emulsion of acrylic polymer,
(ii) about 1 part by volume of aqueous emulsion of vinyl acetate/acrylic copolymer; and
(d) aqueous top-coat nail polish composition comprising:
(i) about 3 parts by volume of aqueous solution of polyurethane resin, and
(ii) about 1 part by volume of aqueous emulsion of vinyl acetate/acrylic copolymer.

12. The system of aqueous nail polish compositions of claim 9 wherein at least one of the following conditions obtains:
(a) said aqueous emulsion of acrylic polymer includes acrylic polymer in an amount not exceeding about 50 wt %;
(b) said aqueous emulsion of vinyl acetate/acrylic copolymer includes about 47 to 48 wt % vinyl acetate/acrylic copolymer and about 52 to 53 wt % water; and
(c) said aqueous solution of polyurethane resin includes about 35 to 40 wt % polyurethane resin.

* * * * *